United States Patent [19]

King, Jr. et al.

[11] Patent Number: 4,707,444
[45] Date of Patent: Nov. 17, 1987

[54] METHOD FOR PREDICTING THE ACCEPTABILITY OF COARSELY GROUND BEEF

[75] Inventors: A. Douglas King, Jr., Martinez; Patricia S. Nassos-Stalder, Redwood City, both of Calif.

[73] Assignee: The United States of America as represented by the Secretary of Agriculture, Washington, D.C.

[21] Appl. No.: 742,485

[22] Filed: Jun. 7, 1985

[51] Int. Cl.$^4$ .................. C12Q 1/32; C12Q 1/22; G01N 33/12
[52] U.S. Cl. .................................. 435/26; 435/31; 426/231
[58] Field of Search ................ 435/31, 26, 810; 426/55, 56, 231, 59

[56] References Cited

U.S. PATENT DOCUMENTS 4,310,625  1/1982  Modrovich .................. 435/26
4,351,899  9/1982  Owen .......................... 435/26

FOREIGN PATENT DOCUMENTS 0208675  4/1984  German Democratic Rep. ... 435/26
0138398  10/1980  Japan ............................. 435/26

OTHER PUBLICATIONS

Jaye et al., Food Technology (1962), No. 5, vol. 16, pp. 95–98.
P. S. Nassos, A. Douglas King, Jr., and Allan E. Stafford, "Relationship Between Lactic Acid Concentration and Bacterial Spoilage in Ground Beef", *Applied and Environmental Microbiology* 46(4): 894–900 (1983).
P. S. Nassos, J. E. Schade, A. D. King, Jr., and A. E. Stafford, "Comparison of HPLC and GC Methods for Measuring Lactic Acid In Ground Beef", *Journal of Food Science* 49(3): 671–674 (1984).
H. Salwin and J. F. Bond, "Quantitative Determination of Lactic Acid and Succinic Acid in Foods by Gas Chromatography", *Journal of the Association of Official Agricultural Chemists* 52: 41–47 (1969).
M. D. Pierson, D. L. Collins-Thompson, and Z. J. Ordal, "Microbiologcial, Sensory and Pigment Changes of Aerobically and Anaerobically Packaged Beef", *Food Technology*, Oct. 1970, pp. 129–133.

*Primary Examiner*—Esther M. Kepplinger
*Assistant Examiner*—William J. Herald
*Attorney, Agent, or Firm*—M. Howard Silverstein; David G. McConnell; Margaret A. Connor

[57] ABSTRACT

A method for predicting the future acceptability of coarsely ground beef after regrinding and aerobic storage under specified conditions of time and temperature by measurement of the concentration of lactic acid in the sample is described. The method includes the steps of setting up a data base which relates the values of the initial concentration of lactic acid in samples of coarsely ground beef to odor acceptability of the samples after regrinding and aerobic storage for specified conditions of time and temperature, and measuring the initial lactic acid in the test sample and predicting future acceptability with reference to the data base. Based on the prediction value, a decision is made whether the beef is acceptable for the intended purpose.

3 Claims, 1 Drawing Figure

METHOD FOR PREDICTING THE ACCEPTABILITY OF COARSELY GROUND BEEF

BACKGROUND OF THE INVENTION

This invention relates to and has among its objects the provision of a novel method for predicting the future acceptability of coarsely ground beef after regrinding and aerobic storage under specified conditions of time and temperature by measurement of the concentration of lactic acid in the sample prior to regrinding and storage.

Hamburger use is extensive in the United States. In 1982, Federally inspected ground beef totaled 3.2 billion pounds. A method for predicting the acceptability of ground beef could result in considerable economic savings by minimizing losses due to spoilage of ground beef. For example, a means to predict spoilage is important to ensure purchase of high quality meat for retail sale, for institutional use including the school lunch program and the military, and the like because it would ensure purchase of high quality meat by permitting judgment of purchase on predicted acceptability. Another important use of such a prediction method is so that a retailer, institution, etc. can make judgments for handling procedures of ground beef currently in stock so that quality control standards are met and losses due to spoilage are minimized. Another important use would be for regulatory purposes.

Refrigerated beef stored under aerobic conditions has only limited shelf life due to growth of aerobic spoilage flora in the meat, usually dominated by Pseudomonas spp., which are proteolytic bacteria and cause the "sweet-rotten" odor associated with spoiled meat. One extensively used handling practice to retard spoilage of ground beef during commercial storage and distribution from a central source is to coarse cut the beef (about 9.5 mm to 19.0 mm diameter die cut) and package it, with or without added carbon dioxide, in oxygen-impermeable casings in about 4.5 kg to 9.0 kg quantities called "chubs" or "keeper" packs. The meat is then shipped and stored under refrigeration until needed. In the anaerobically stored chub packs, there is a predominance of lactic acid-producing bacteria which are non-proteolytic, thus spoilage is retarded. Prior to sale or use, the coarsely ground beef is removed from the oxygen-impermeable casing and is reground in air to give the hamburger texture customarily used for consumption (about 5 mm diameter die cut) and its characteristic red color. This procedure causes the myoglobin in the meat to change from blue color to the red color of oxyhemoglobin associated with fresh meat. Also, the bacterial environment of the beef changes from predominantly lactic acid-producing bacteria to predominantly proteolytic microflora, such as Pseudomonas spp., and thus shelf life of the meat under conditions of aerobic storage is limited. Pseudomonas spp. which cause the "sweet-rotten" odor of spoiled meat grow under aerobic conditions which do not promote the growth of lactic acid bacteria.

A number of procedures have been proposed to correlate microbial and biochemical assays with meat spoilage but these have met with limited success. Bacterial counts are genenerally thought to be an indicator of early spoilage, with "off" odors becoming apparent when bacterial numbers reach approximately $10^7$ cells per gram of meat. Unfortunately, bacterial counts are time consuming, taking from 5 to 10 days for accurate assessment of psychrotrophic bacteria. There is also some disagreement as to whether total bacterial counts correlate with organoleptic appraisal of the meat product and whether total or differential counts can be used to assess future acceptability. Proteolytic bacteria, such as some Pseudomonas spp., will cause spoilage at lower numbers than lactic acid-producing organisms which can produce "acid/sour" spoilage due to buildup of lactic acid. Several tests other than total bacterial counts have been tried to measure the microbial quality of processed meat. These tests, which include indicator dye methods, extract release volume, release of ammonia, pH, and titratable acidity, have proven to be of limited value and are not in use. Reductase tests, using certain dyes which act as hydrogen acceptors in measurement of dehydrogenase levels, have been tried for determining spoilage in beef. These tests are not feasible for use with ground or minced beef products due to release of cellular reductones during the grinding process.

The relationship (positive correlation) between lactic acid concentration and bacterial spoilage in coarsely ground beef stored under anaerobic conditions where lactic acid bacteria predominate and where the activity of proteolytic spoilage bacteria is minimal was reported by P. S. Nassos et al. in *Applied and Environmental Microbiology* 46(4): 894–900 (1983). Spoilage was determined by organoleptic acceptability testing. The increased lactic acid concentration which develops in coarsely ground beef in oxygen-impermeable casings was thought by researchers to be partially responsible for prohibiting growth of Pseudomonas spp. and other proteolytic microflora. The relationship between lactic acid and growth of proteolytic Gram-negative microflora, however, appears to be complex. Research by others gives evidence of lactic acid as a possible promotor, rather than inhibitor of growth, as some Pseudomonas spp. will utilize glucose preferentially, but once glucose is exhausted in the media, will utilize lactic acid and amino acids for growth. Because of the complex and conflicting information between lactic acid and proteolytic bacteria, none of the known research provided any suggestion as to how to predict spoilage in coarsely ground beef once it has been reground and stored under aerobic conditions where proteolytic bacteria (Pseudomonas spp.) dominate the microflora.

SUMMARY OF THE INVENTION

The invention described herein provides a method for predicting the future acceptability of coarsely ground beef after regrinding and storage under predetermined aerobic conditions by measurement of the concentration of the lactic in the sample prior to regrinding and storage. Surprisingly, although spoilage during storage of ground beef in air results from proteolytic bacteria rather than lactic-acid producing bacteria, acceptability of ground beef in the aerobic state can be predicted from the initial concentration of lactic acid in the sample, that is, the concentration in the sample prior to storage for the predetermined conditions. This method works whether the meat is stored anaerobically prior to aerobic storage or whether the ground beef is obtained directly from the processing plant without anaerobic storage. The prediction method of the invention also works whether the lactic acid is from an animal or bacterial source or combination thereof.

The method of the invention includes: step (1) setting up a data base which relates the values of the initial concentration of lactic acid in samples of coarsely ground beef to odor acceptability of the samples after regrinding and storage under aerobic conditions for a set period of time and temperature., and step (2) measuring the initial lactic acid in the test sample and predicting future acceptability, as determined by odor acceptability, with reference to the data base of step (1). Based on the prediction value of step (2), a decision is made whether the beef will be acceptable for the intended purpose.

In accordance with this discovery, it is an object of the invention to provide a method for predicting acceptibility of coarsely ground beef that will be held under a known set of storage conditions such as regrinding and repackaging which occurs in normal commercial handling practices.

It is also an object of the invention to provide a means to predict spoilage in the beef so as to ensure selection and/or purchase of high quality meat.

It is a further object of the invention to provide a method of quality control of ground beef and to provide a quick, reliable method of determining incipient spoilage in ground beef and thereby preventing economic losses of meat that should be rapidly used due to a predicted shorter shelf life.

A still further objective of the invention is to provide a method to predict acceptability of ground beef for use by regulators of the meat industry.

Other objects and advantages of this invention will become readily apparent from the ensuing description.

DETAILED DESCRIPTION OF THE INVENTION

Figure 1:
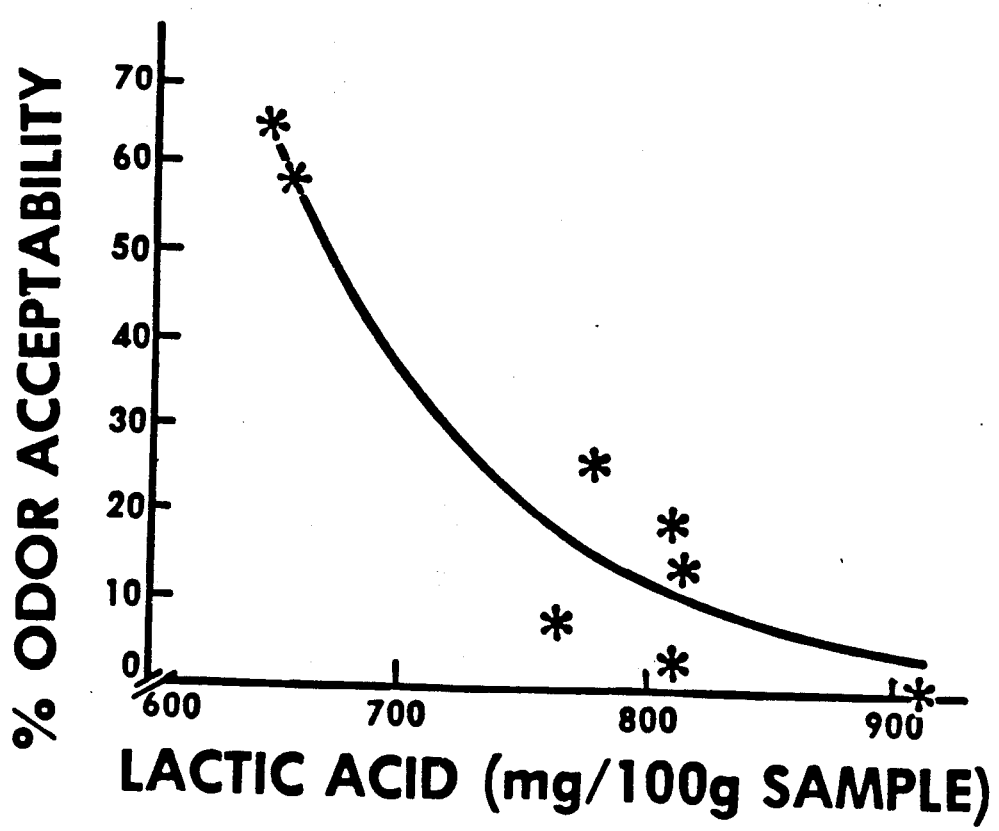
FIG. 1 is a graph of initial lactic acid concentration of anaerobically stored lean grade beef and percent odor acceptability determined after 6 days of aerobic storage at 7° C. The regression curve was fitted to the data with the equation: $Y = ae^{bX}$, where Y represents % odor acceptability, X represents lactic acid concentration, a equals 507079, and b equals $-0.014$.

Step 1. Setting up a data base which relates initial concentration of lactic acid in coarsely ground beef to odor acceptability of the samples after regrinding and aerobic storage for a set period of time and temperature.

The data base to predict acceptability of coarsely ground beef is prepared as follows:

Step (a). The initial concentration of total lactic acid of samples of coarsely ground beef is measured. This initial value may be obtained on fresh coarsely ground beef or on a chub pack (anaerobically stored coarsely ground beef). The term "initial value of lactic acid" is defined as the value obtained prior to regrinding and aerobic storage under the specified conditions.

Samples to be used in setting up the data base are selected as follows: samples with varying initial lactic acid values which are obtained by selecting different pieces of meat; samples stored anerobically and subsampled at different times of storage so that different values of lactic acid are present; or a combination of these two procedures.

For this invention, the term "coarsely ground beef" is defined as meaning beef which has been ground to a range of about 9.5 to 19.0 mm diameter die cut or the equivalent. Lactic acid ($CH_3CHOHCOOH$) includes both D- and L-lactic acid isomers. Lactic acid is present in coarsely ground beef from two sources, as part of the composition of the animal tissue and from production by lactic acid-producing bacteria during anaerobic storage. Such bacteria include species from the genera Lactobacillus, Leuconostoc, Streptococcus, and Brochothrix. As stated above, the prediction method of the invention works whether the lactic acid is from an animal or bacterial source or a combination thereof. Lactic acid forms salts with many metals and may exist in ground beef in the salt form, e.g., sodium, zinc, and calcium salts. The method still works however because during analyses these salts are converted to lactic acid and thus measured.

Methods to measure total lactic acid in coarsely ground beef are known in the art and include enzymatic methods, gas chromatography (GC), and high performance liquid chromatography (HPLC). A detailed description and comparison of GC and HPLC methods for measuring lactic acid in coarsely ground beef is reported by P. S. Nassos et al., *Journal of Food Science* 49(3): 671-674 (1984) which is hereby incorporated by reference. Where speed of analysis is desired, the HPLC or enzymatic method is preferred as lactic acid can be determined in about one hour versus 12 hours for the GC method.

In the HPLC method, the coarsely ground beef sample is reground to a size of about 5 mm in diameter, homogenized, and filtered. An internal standard, e.g., L-tartaric acid, is added to the filtrate and the filtrate mixed with perchloric acid, and filtered to remove the protein. Prior to injection into the HPLC, the filtrate is filtered through a 4.5 micron membrane filter. Analysis is carried out using a HPLC column suitable for organic acid analysis, such as Aminex HPX-87H ion exclusion column (Bio-Rad Laboratories, Berkeley, CA), ORH-801 organic acid column (Rainin Instrument Co., Woburn, MA), or Alltech organic acid column OA-1000 (Alltech Associates Inc., Deerfield, IL). Lactic acid is calculated from its peak height or area relative to that of the internal standard.

Step (b). Odor acceptability of the samples of step (a) is measured after regrinding and aerobic storage for the specified conditions of time and temperature. As stated above, usual handling practices for commercial distribution and use (or sale) of ground beef involve storage of the beef for a narrow range of conditions of time and temperature. In most cases, the coarsely ground beef is shipped and stored in anaerobically wrapped chub packs under refrigeration (about 0°-10° C.) up to not more than about 3 weeks and then reground to normal hamburger texture (cutter diameter about 4-6 mm) and held under aerobic conditions with refrigeration (about 0°-10° C.) for short periods (about 1-4 days) until use or sale. In some cases, fresh coarsely ground beef may be distributed. The method of the invention may be used for any storage conditions which include aerobic storage. The critical feature is that the data base be set up to include the conditions under which the test samples will be handled.

Determination of odor acceptability using a sensory panel is described by P. S. Nassos et al., *Appl. Environ. Microbiol.*, supra, p. 895. In this procedure, the sample of coarsely ground beef is presented in glass-stoppered 125-ml Erlenmeyer flasks wrapped in tissue to mask appearance. The odor samples are judged in air-conditioned booths under 7.5-W green bulbs. Sample rating is determined with a standard nine-point hedonic scale (a score of 9, like extremely; a score of 5, neither like nor dislike; and a score of 1, dislike extremely). Panel members are also asked to note whether the meat sample is acceptable or unacceptable. Percent odor acceptability of each sample is obtained from the panel judgments by calculation from the ratio of acceptable scores to the total number of judgments, or by the average hedonic scores. Either value can be used to relate odor acceptability to lactic acid concentration.

Step (c). A graphical representation such as a graph or regression equation which relates the initial values of lactic acid obtained in step (a) with the values for odor acceptability after the specified storage period obtained in step (b) is prepared. In this step, the values for lactic acid of step (a) and the values for odor acceptability of step (b) are related such as by plotting a graph of odor acceptability versus lactic acid concentration or by determining an equation for the regression curve of odor acceptability versus lactic acid concentration.

Step (d). Using the graph obtained in step (c), an uppermost limit or range of lactic acid is selected which meets odor acceptability requirements based on the requirements of the user.

Step 2. Prediction of acceptability of coarsely ground beef in test samples after aerobic storage under specified conditions of time and temperature.

To predict the future acceptability of coarsely ground beef in the test sample after aerobic storage for specified conditions of time and temperature, the concentration of total lactic acid in the sample is determined by any of the methods described above and the value compared with the graphical representation prepared in step (1). Given the value of the lactic acid in the test sample, one can determine the odor acceptability of the sample after the set of storage conditions. Where the coarsely ground beef is being purchased or used for uses which require different storage conditions, a data base is set up for each storage condition of interest and then the test sample is evaluated for any of the conditions.

Based on the predicted acceptability over a given shelf life as determined by odor acceptability in step (2), a decision is made whether the beef will have an acceptable shelf life for the intended purpose. The criteria for determining this include a specific set of storage conditions (time and temperature) for purchase, for rapid use (or sale) of stock on hand, regulatory purposes, or for quality control use. The value of lactic acid selected as the upper limit depends upon the purpose of the test as described above or the intended use, e.g., for institutional use, for canning, and the like.

One use of the method of the invention is to predict future acceptability of coarsely ground beef using the method of the invention with a test device which measures lactic acid. This device is used to obtain the initial lactic acid values to set up the data base of step (1) and/or obtain the lactic acid values of test samples according to step (2). In either case, the device contains stabilized lactic dehydrogenase enzyme (D and L), a source of nicotinamide adenine dinucleotide (NAD) to convert lactic acid to pyruvic acid, and a color-producing reagent such as phenylhydrazine to allow measurement of the pyruvic acid in the test device visually or by instruments such as a colorimeter. Lactic acid is converted by the enzyme and NAD into pyruvic acid which reacts with phenylhydrazine to form a colored phenylhydrazone. The lactic acid concentration of the beef is determined from the color intensity developed on the test device. The color intensity of the test sample is compared to a predetermined data base which relates lactic acid concentration determined colorimetrically under the same conditions with future acceptability of the meat as determined by odor acceptability as described above.

The method of the invention is further demonstrated by the following illustrative examples. Theses examples are intended only to further illustrate the invention and are not intended to limit the scope of the invention which is defined by the claims.

EXAMPLE 1

Determination of Initial Lactic Acid Concentration

Sample preparation

Anaerobic storage. Nine coarsely ground beef samples (12.7 mm diameter die cut) packaged in 9 kg (20 lb), sausage-like, chub packs with relatively low oxygen permeability (40 cc $O_2 \cdot m^{-2} \cdot d^{-1} \cdot atm^{-1}$ at 22.8° C.) were used in this study. At the time of procurement samples were stored in the chub packs for less than 1 week. Three samples each of very lean (12–15%), lean (16–19%), and medium fat (26–28%) were examined. On arrival at the laboratory, one-third of each sample was reground using a Hobart food grinder (Kitchen Aid, model K5-A, Hobart Mfg. Co., Troy, OH) with a 4.8 mm hole size plate. Portions of these reground samples were analyzed within 2 hours of procurement for lactic acid concentration, total aerobic bacterial count, number of Gram-positive organisms (used as an indicator of lactic acid-producing bacteria present), and pH. The remaining two-thirds of each coarsely ground sample was resealed in oxygen-impermeable wrap and returned to refrigeration at 7° C. A second and third portion from the chub packs were reground after 1 and 2 weeks of anaerobic storage and the analyses repeated. Prior to regrinding of these samples, small portions of meat suspected of being exposed to oxygen from the previous pack opening were discarded.

Aerobic storage. Reground beef samples from the chub packs not used for the initial analyses were formed into long strips of uniform depth and width (25 mm by 100 mm). These strips of reground beef were wrapped in one layer of 0.5 mil low density polyethylene plastic with a relatively high oxygen permeability (420 cc $O_2 \cdot m^{-2} \cdot d^{-2} \cdot atm^{-1}$ at 23° C. for 1.0 mil thickness) and stored at 7° C. After aerobic storage for 1, 3, and 6 days, portions of the reground samples were analyzed for the same parameters described above. In addition, sensory appraisals for odor and appearance were conducted on the lean grade samples.

Bacteriology

Aerobic bacterial counts and calculations of the percentage of Gram-positive organisms to total number present were conducted as described by P. S. Nassos et al., *Appl. Environ. Microbiol.*, supra, p. 895. The percentage of Gram-positive organisms in the samples was used as an indicator of the proportion of lactic acid-producing bacteria present.

Lactic acid analysis

Approximately 400 grams of ground beef for lactic acid analysis was first mixed by homogenizing for 1 minute in a Cuisinart food processor (model DLC-10) with a metal chopping disk. A beef extract was prepared from 50 grams of the homogenized meat and 0.2

N HCl as follows: A 25-g subsample was added to 215 ml of 0.2 N HCl and 10 ml of an internal standard solution containing 72 mg of glutaric acid. This mixture was homogenized, centrifuged, filtered, and adjusted to pH 10. Ten ml of the filtrate was lyophilized. After lyophilization, the sample was esterified with boron trifluoride (15% [wt/vol]) in propanol (BF$_3$-propanol) according to the procedure of Salwin and Bond (*Journal of the Association of Official Agricultural Chemists* 52: 41–47 (1969), except the amounts of BF$_3$-propanol and saturated $(NH_4)_2SO_4$ used in the assay were increased to 10 ml, and CHCl$_3$ was increased to 5 ml.

The resulting propyl derivatives of lactic and glutaric acid were measured with a Hewlett-Packard gas chromatograph (model 5720A) equipped with a flame ionization detector. The glass column was packed with 80/100 mesh Chromosorb W.-H.P. coated with 10% AT-1000 (Altech Associates, Deerfield, IL). Helium flow at the detector was 30 ml/min, and the detector and injector were operated at 300 and 225° C., respectively. The column was programmed from 100 to 180° C. at 8° C./min. So as not to interfere with subsequent analysis, higher-molecular-weight fatty acid esters were removed from the column by programming to 240° C. and holding this temperature for 6 min. The peaks of interest were measured quantatively with a Hewlett-Packard 3390A integrator. Samples were run in triplicate and the results averaged.

The results of the above analyses for the lean grade samples are reported in Table 1.

TABLE 1

| Lactic Acid (mg/100 g sample) | Aerobic Bacteria Plate Counts (Log$_{10}$ of total) | Gram-positive Organisms (% of total microflora) | Odor Acceptability (%) |
| --- | --- | --- | --- |
| 644.1 | 4.663 | 23 | 62.5 |
| 809.6 | 6.529 | 47 | 17.5 |
| 776.0 | 6.356 | 63 | 25.0 |
| 652.0 | 4.332 | 19 | 57.5 |
| 813.7 | 6.991 | 44 | 12.5 |
| 810.6 | 6.954 | 66 | 2.5 |
| 764.7 | 5.568 | 51 | 7.5 |
| 909.0 | 6.851 | 85 | 0 |

EXAMPLE 2

Determination of Odor Acceptability

Sensory appraisal

Lean grade samples described in Example 1 were rated by a 20-member sensory panel for odor and appearance after 1, 3, and 6 days of aerobic storage which followed sample procurement and 0, 1, and 2 weeks of anerobic storage. Sample rating was determined with a standard nine-point hedonic scale (a score of 9, like extremely; a score of 5, neither like nor dislike, a score of 1, dislike extremely). Panel members were also asked to note whether the meat sample was acceptable or unacceptable in both odor and appearance. Results of the two odor acceptability procedures had a correlation coefficient of 0.78. Thus, either method can be used. Each sample was appraised twice within a 6-hour period, within 2 hours after removal from its package. A portion of the meat sample was presented in glass-stoppered 125-ml Erlenmeyer flasks wrapped in tissue to mask appearance. The odor samples were judged in air-conditioned booths under 7.5-W green bulbs. The results for odor acceptability after 6 days of aerobic storage subsequent to 0, 1, and 2 weeks of anaerobic storage are presented in Table 1.

EXAMPLE 3

Setting up the Data Base of the Relationship of Odor Acceptability and Lactic Acid Concentration in Coarsely Ground Beef To determine the relationship and prediction equation of acceptability after specified aerobic storage conditions of time and temperature of ground beef as a function of lactic acid concentration of the sample, a graph was made of the initial value of the concentration of lactic acid in the samples obtained in Example 1 and the percent odor acceptability of the samples of lean grade coarsely ground beef after 6 days of aerobic storage at 7° C. described in Example 2. The equation used for the regression curve representing percent odor acceptability on day 6 (Y) versus initial lactic acid concentration following anaerobic storage (X) is as follows: $Y = ae^{bX}$ ($R^2 = 0.88$ and $P < 0.01$), where Y represents % odor acceptability, X represents lactic acid concentration, a equals 50,709, and b equals $-0.014$. Correlation of the data is 0.916. The slope$=0.252$ and the intercept$=217$. The regression equation was derived from a non-linear regression computer program using Marquardt's procedure. The curve is shown in FIG. 1. The stars represent the data points.

EXAMPLE 4

Prediction of Future Acceptability of Coarsely Ground Beef from Lactic Acid Concentration The data base prepared in Example 3 is used to predict the future acceptability of test samples within the limits of the data base as follows. The initial value of lactic acid of the test sample is measured. Percent odor acceptability for the sample after regrinding and aerobic storage conditions of the data base is determined from the graph of FIG. 1 or the regression equation given in Example 3. As stated above, what value of percent odor acceptability to use to determine whether or not the beef is acceptable depends on the intended use of the lot of the meat selected by the testor. For example, purchase specifications, quality control, or regulatory purposes could require different final quality as measured by percent odor acceptability. Once this value is selected, then using the data base, whether or not the test sample meets this requirement is determined from the lactic acid value of the sample by comparison to the data base.

For example, with reference to FIG. 1, if the limit of acceptance is 50% odor acceptability, then a lactic acid value in the test sample of greater than 659 mg/100 g of sample would mean that the sample would be unacceptable. Similarly, a 60% acceptability limit would correspond to 646 mg lactic acid per 100 g of the test sample and 20% acceptability would correspond to 724 mg lactic acid per 100 g of the test sample.

EXAMPLE 5

Lactic Acid Enzyme Test Device

Lactic acid is measured by a device or in solution by a colorimetric test for measurement as follows: stabilized lactate dehydrogenose plus nicotinamide adenine dinucleotide are used to convert lactic acid to pyruvic acid. A color reaction between pyruvic acid and phenylhydrazine is used to visualize the results of the lactic to pyruvic acid conversion and gives a quantitative analysis of the amount of lactic acid in the ground beef sample. Ideally the device is a test strip or stick that is used and compared with a color chart to relate the amount of color developed to concentration of lactic acid in the sample.

It is understood that the foregoing detailed description is given merely by way of illustration and that modifications and variations may be made therein without departing from the spirt and scope of the invention.

Having thus described out invention, we claim:

1. A method for predicting the future acceptability of coarsely ground beef in a test sample subsequent to regrinding and aerobic storage for specified conditions of time and temperature, which comprises:
  (a) setting up a data base which relates initial concentration of lactic acid in coarsely ground beef samples to odor acceptability of said samples after regrinding and aerobic storage for specified conditions of time and temperature by treating as follows:
    (i) measuring said initial concentration of lactic acid in said samples of coarsely ground beef;
    (ii) regrinding said samples of step (i) to about 4-6 mm and aerobically storing for specified conditions of time and temperature;
    (iii) measuring said odor acceptability of said stored samples of step (ii);
    (iv) preparting a graphical representation or equation which correlates said initial concentration of lactic acid in said samples with said values for odor acceptability of said stored samples; and
  (b) measuring the initial lactic acid in a test sample of coursely ground beef and obtaining a value for odor acceptability of said test sample under said predetermined storage conditions by comparison with the data base prepared in step (a) and predicting the acceptability of said test sample.

2. The method of claim 1 wherein said samples are stored under anaerobic conditions prior to said aerobic storage.

3. The method of claim 1 wherein said initial concentration of lactic acid in said coarsely ground beef is measured by a step which comprises applying stabilized lactate dehydrogenase, a source of nicotinamide adenine dinucleotide (NAD) to convert lactic acid to pyruvic acid, and a color-producing reagent which allows colorimetric measurement of said converted pyruvic acid and measuring the degree of color change to determine the concentration of lactic acid.

* * * * *